United States Patent
Walker et al.

(10) Patent No.: US 9,540,662 B2
(45) Date of Patent: *Jan. 10, 2017

(54) METHODS AND COMPOSITIONS FOR PRODUCING SQUALENE USING YEAST

(71) Applicant: NUCELIS LLC, San Diego, CA (US)

(72) Inventors: Keith A. Walker, San Diego, CA (US); Mark E. Knuth, Poway, CA (US); Noel M. Fong, San Diego, CA (US); Peter R. Beetham, Carlsbad, CA (US)

(73) Assignee: NUCELIS LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/926,288

(22) Filed: Jun. 25, 2013

(65) Prior Publication Data

US 2014/0134696 A1    May 15, 2014

Related U.S. Application Data

(63) Continuation of application No. 12/952,161, filed on Nov. 22, 2010, now Pat. No. 8,470,568.

(60) Provisional application No. 61/263,775, filed on Nov. 23, 2009.

(51) Int. Cl.
| | |
|---|---|
| *C12P 5/02* | (2006.01) |
| *C12N 15/52* | (2006.01) |
| *C12N 15/81* | (2006.01) |
| *C12P 5/00* | (2006.01) |
| *C12R 1/73* | (2006.01) |

(52) U.S. Cl.
CPC .............. *C12P 5/026* (2013.01); *C12N 15/52* (2013.01); *C12N 15/815* (2013.01); *C12P 5/007* (2013.01); *C12R 1/73* (2013.01)

(58) Field of Classification Search
None
See application file for complete search history.

(56) References Cited

U.S. PATENT DOCUMENTS

| | | | | |
|---|---|---|---|---|
| 4,628,033 | A | * 12/1986 | DeZeeuw | ............... 435/254.2 |
| 2007/0015237 | A1 | * 1/2007 | Bailey et al. | ............... 435/67 |

OTHER PUBLICATIONS

Chu et al. Biochim Biophys Acta. Dec. 2007;1774(12):1571-81. Epub Sep. 21, 2007.*

* cited by examiner

*Primary Examiner* — Christian Fronda
(74) *Attorney, Agent, or Firm* — Acuity Law Group, PC; Michael A. Whittaker

(57) ABSTRACT

Provided herein compositions and methods for producing isoprenoids, including squalene. In certain aspects and embodiments provided are genetically converted yeast and uses therefore. In some aspects and embodiments, the genetically converted yeast produce isoprenoids, preferably squalene. Also are provided methods of producing squalene using a genetically converted yeast or a non-genetically converted yeast. The invention also provides squalene produced by genetically converted yeast or non-genetically converted yeast.

17 Claims, No Drawings

SEQUENCE LISTING

```
<160> NUMBER OF SEQ ID NOS: 6

<210> SEQ ID NO 1
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="5' CY3"
<220> FEATURE:
<221> NAME/KEY: modified_base
<222> LOCATION: (41)..(41)
<223> OTHER INFORMATION: /note="DMT dC CPG"

<400> SEQUENCE: 1
cgaggtctgt acggccagaa ccgagatcct attgaggagg c                         41

<210> SEQ ID NO 2
<211> LENGTH: 41
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="5' CY3"
<220> FEATURE:
<221> NAME/KEY: modified_base
<222> LOCATION: (41)..(41)
<223> OTHER INFORMATION: /note="DMT dC CPG"

<400> SEQUENCE: 2
cctcctcaat aggatctcgg ttctggccgt acagacctcg c                     41

<210> SEQ ID NO 3
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="5' CY3"
<220> FEATURE:
<221> NAME/KEY: modified_base
<222> LOCATION: (43)..(43)
<223> OTHER INFORMATION: /note="idC"

<400> SEQUENCE: 3
gaactcaccg cgacgtctgt cgagaagttt ctgatcgaaa agc                   43

<210> SEQ ID NO 4
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="5' CY3"
<220> FEATURE:
<221> NAME/KEY: modified_base
<222> LOCATION: (1)..(1)
<223> OTHER INFORMATION: /note="DMT dC CPG"
<220> FEATURE:
<221> NAME/KEY: modified_base
<222> LOCATION: (44)..(44)
<223> OTHER INFORMATION: /note="idC"

<400> SEQUENCE: 4 cctttttcgat cagaaacttc tcgacagacg tcgcggtgag ttcc                 44

<210> SEQ ID NO 5
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="5' CY3"
<220> FEATURE:
<221> NAME/KEY: modified_base
```

-continued

```
<222> LOCATION: (44)..(44)
<223> OTHER INFORMATION: /note="idC"

<400> SEQUENCE: 5
ctcaccgcga cgtctgtcga gaagtttctg atcgaaaagt tcgc        44

<210> SEQ ID NO 6
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(1)
<223> OTHER INFORMATION: /note="5' CY3"
<220> FEATURE:
<221> NAME/KEY: modified_base
<222> LOCATION: (44)..(44)
<223> OTHER INFORMATION: /note="idC"

<400> SEQUENCE: 6 cgaactttc gatcagaaac ttctcgacag acgtcgcggt gagc         44
```

METHODS AND COMPOSITIONS FOR PRODUCING SQUALENE USING YEAST

RELATED PATENT APPLICATIONS

This application is a continuation application of U.S. patent application Ser. No. 12/952,161, filed Nov. 22, 2010, which claims priority to U.S. Provisional App. No. 61/263,775, entitled "Methods and Compositions for Producing Squalene Using Yeast", filed Nov. 23, 2009, which is incorporated herein by reference in its entirety and for all purposes.

SEQUENCE LISTING

The instant application contains a Sequence Listing which has been submitted electronically in ASCII format and is hereby incorporated by reference in its entirety. Said ASCII copy, created on Jan. 24, 2014, is named CIBUS001CT_SequenceListing.txt and is 3 kilobytes in size.

FIELD OF THE INVENTION

Provided are methods and compositions for producing isoprenoids such as squalene using yeast.

BACKGROUND OF THE INVENTION

The following description of the background of the invention is provided simply as an aid in understanding the invention and is not admitted to describe or constitute prior art to the invention.

Isoprenoids, such as squalene, are commercially important types of lipids. They have excellent lubricity, oxidative stability, low pour points, low freezing points, high flash points, and facile biodegradability. Squalene is currently produced by extraction from olive oil or cold water shark liver oil at a high unit cost. Because of the high unit cost, economically feasible uses for squalene and squalene (the fully hydrogenated derivative of squalene) are in small market applications such as watch lubricants, pharmaceutically/nutraceuticals, cosmetics, perfumes and as chemical intermediates for high-value products.

There exist, however, significant potential markets for biodegradable lubricants, lubricant additives, and hydraulic fluids. Biodegradability of these products is particularly important for environmentally sensitive applications, such as agricultural applications, or where considerable lubricant or hydraulic fluids may be lost to the environment. The potential markets for biodegradable lubricants, lubricant additives, and hydraulic fluids are quite large, estimated to be on the order of five million metric tons per annum.

Biodegradable lubricants, lubricant additives, and hydraulic fluids derived from vegetable and animal fats and oils are available, but they have drawbacks. They typically solidity at relatively high temperatures (i.e., they solidity in cold weather) and have flash points that are too low for use in hot conditions, (i.e., they break down or combust under normal hot engine conditions).

Thus, a cost effective method of production of squalene is desired that would allow for large-scale manufacturing and widespread use of squalene and squalane in biodegradable lubricants, lubricant additives, and hydraulic fluids.

Chang et al., (*Appl. Microbiol. Biotechnol.*, 2008, 78, 963-72) discloses the discovery of a wild type yeast, *Pseudozyma* sp. JCC207, that produces "a large amount of squalene and several polyunsaturated fatty acids." Chang et al. describe isolating *Pseudozyma* sp. JCC207 from seawater collected near Guam, USA, and are unsure whether *Pseudozyma* sp. JCC207 is a new species or a variant of *P. regulosa* or *P. aphidis*. In the article, "the efficiency of squalene production [of *Pseudozyma* sp. JCC207] was investigated under different conditions."

Dow AgroSciences LLC, *Using Yeast Fermentatin to Produce Cost-Effective and Biodegradable Lubricants*, http://statusreports.atp.nist.gov/reports/95-01-0148PDF.pdt, discloses that "[t]he company proposed to use genetic engineering to alter the metabolic characteristics of an oleaginous (oily) yeast to increase the yeast's ability to produce isoprenes through biosysnthesis." Specifically, four enzymes were targeted: ACCase, hydroxymethylglutaryl CoA reductase (HNGR), squalene synthetase, and squalene epoxidase.

U.S. Pat. No. 5,460,949 discloses "[a] method increasing the accumulation of squalene and specific sterols in yeasts." In particular, it is disclosed that "[s]qualene and sterol accumulation is increased by increasing the expression level of a gene encoding a polypeptide having the HMG-CoA reductase activity."

SUMMARY OF THE INVENTION

The instant invention provides compositions and methods for producing squalene from yeast.

In certain aspects and embodiments, increased amounts of an isoprenoid (for example, squalene) produced by a genetically converted or non-genetically converted yeast may be the result of mutating, modifying and/or altering the activity of one or more enzymes within the isoprenoid biosynthesis pathway. For example acetyl-CoA carboxylase (or "ACCase"), HMG-CoA reductase, squalene epoxidase, squalene synthase, ATP citrate synthase, mevalonate kinase (e.g., *Y. lipolytica* mevalonate kinase (Genolevures YAL10B16038g)), glycerol kinase (e.g., *Y. lipolytica* glycerol kinase (Genolevures YAL10B16038g)), and/or 5-aminolevulinate synthase (e.g., encoded by *Saccharomyces cerevisiae* HEM1 gene) may be modified, mutated or have altered activity.

In some preferred embodiment, a genetically converted yeast expressing a modified enzyme is produced by introducing a mutation in the enzyme through use of a gene repair oligonucleobase as described herein. In some embodiments provided methods include introducing a gene repair oligonucleobase containing a specific mutation for a target gene of interest into a yeast cell by any of the number of methods well-known in the art (e.g., electroporation. LiOAc, biolistics, sheroplasting and/or *Agrobacterium* (see, for example, McClelland, C. M., Chang, Y. C., and Kwon-Chung, K. J. (2005) Fungal Genetics and Biology 42:904-913) and identifying a cell having the mutated enzyme.

In one aspect of the invention, isoprenoids extracted from a genetically converted or non-genetically yeast disclosed herein are provided. In a related aspect, provided is squalene extracted from a genetically converted yeast as described herein.

In another aspect, a method of producing isoprenoids, preferably squalene, is provided. In certain embodiments the method includes providing a genetically converted or non-genetically converted yeast as described herein and extracting squalene from the yeast. In some embodiments, the method includes exposing yeast (either genetically converted or non-genetically converted) to an antifungal agent (for example, an allylamine antifungal agent such as terbinafine) and extracting squalene from the yeast. In some embodiments the method includes exposing a genetically converted yeast such as described herein to an antifungal agent (for example, an allylamine antifungal agent such as terbinafine) and extracting squalene from the yeast. In some embodiments the method includes exposing a non-genetically converted yeast such as described herein to an antifungal agent (for example, an allylamine antifungal agent such as terbinafine) and extracting squalene from the yeast.

In certain embodiments of the methods and compositions disclosed herein that include an antifungal agent (for example, an allylamine antifungal agent such as terbinafine), the antifungal agent (for example terbinafine or other antifungal agent) may be added or present in a concentration at or above about 1 µg/ml; or about 5 µg/ml; or about 10 µg/ml; or about 11 µg/ml; or about 12 µg/ml; or about 12.5 µg/ml; or about 13 µg/ml; or about 15 µg/ml; or about 16 µg/ml; or about 20 µg/ml; or about 25 µg/ml; or about 30 µg/ml; or about 40 µg/ml; or about 50 µg/ml or greater. In certain embodiments of the methods and compositions disclosed herein that include an antifungal agent (for example, an allylamine antifungal agent such as terbinafine), the antifungal agent (for example terbinafine or other antifungal agent) may be added or present in a concentration between about 0.5 to 100 µg/ml; or 0.5 to 50 µg/ml; or 1 to 50 µg/ml; or 5 to 50 µg/ml; or 8 to 50 µg/ml; or 10 to 50 µg/ml; or 12 to 50 µg/ml; or 15 to 50 µg/ml; or 15 to 50 µg/ml; or 25 to 50 µg/ml; or 1 to 25 µg/ml; or 5 to 25 µg/ml; or 10 to 25 µg/ml; or 10 to 20 µg/ml; or 10 to 15 µg/ml.

In one aspect, a genetically converted yeast that produces isoprenoids is provided. In certain embodiments, the genetically converted yeast produces squalene.

In another aspect, provided is a genetically converted yeast, wherein the yeast is genetically converted such that it produces increased levels of squalene as compared to the corresponding native yeast. In certain embodiments of the above aspects of the invention, the genetically converted yeast expresses one or more modified enzymes having one or more mutations. In certain embodiments of the above aspects the expression level of one or more enzymes in the genetically converted yeast is increased or decreased relative to the corresponding native yeast. In related embodiments, the genetically converted yeast expresses one or more modified enzymes having one or more mutations and the expression level of one or more enzymes in the genetically converted yeast is increased or decreased relative to the corresponding native yeast. In certain preferred embodiments a genetically converted yeast as provided herein is genetically converted by introducing a mutation into an enzyme using a gene repair oligobase. In some embodiments a genetically converted yeast as provided herein is genetically converted by introducing one or more mutations at or around the translation start size of a gene encoding an enzyme to increase or decrease expression of the enzyme, for example, as described in U.S. patent application Ser. Nos. 10/411,969 and 11/625,586. In certain embodiments, the enzyme modified in a genetically converted yeast as provided herein includes one or more enzymes selected from the group consisting of acetyl-CoA carboxylase (or "ACCase"), HMG-CoA reductase, squalene epoxidase, squalene synthase, ATP citrate lyase, ATP citrate synthase, mevalonate kinase (e.g., *Y. lipolytica* mevalonate kinase (Genolevures YAL10B16038g)), glycerol kinase (e.g., *Y. lipolytica* glycerol kinase (Genolevures YAL10F00484g)) and 5-aminolevulinate synthase.

A nucleobase comprises a base, which is a purine, pyrimidine, or a derivative or analog thereof. Nucleosides are nucleobases that contain a pentosefuranosyl moiety, e.g., an optionally substituted riboside or 2'-deoxyriboside. Nucleosides can be linked by one of several linkage moieties, which may or may not contain phosphorus. Nucleosides that are linked by unsubstituted phosphodiester linkages are termed nucleotides. "Nucleobases" as used herein include peptide nucleobases, the subunits of peptide nucleic acids, and morpholine nucleobases as well as nucleosides and nucleotides.

An oligonucleobase is a polymer of nucleobases, which polymer can hybridize by Watson-Crick base pairing to a DNA having the complementary sequence. An oligonucleobase chain has a single 5' and 3' terminus, which are the ultimate nucleobases of the polymer. A particular oligonucleobase chain can contain nucleobases of all types. An oligonucleobase compound is a compound comprising one or more oligonucleobase chains that are complementary and hybridized by Watson-Crick base pairing. Nucleobases are either deoxyribo-type or ribo-type. Ribo-type nucleobases are pentosefuranosyl containing nucleobases wherein the 2' carbon is a methylene substituted with a hydroxyl, alkyloxy or halogen. Deoxyribo-type nucleobases are nucleobases other than ribo-type nucleobases and include all nucleobases that do not contain a pentosefuranosyl moiety.

An oligonucleobase strand generically includes both oligonucleobase chains and segments or regions of oligonucleobase chains. An oligonucleobase strand has a 3' end and a 5' end. When an oligonucleobase strand is coextensive with a chain, the 3' and 5' ends of the strand are also 3' and 5' termini of the chain.

The term "gene repair oligonucleobase" is used herein to denote oligonucleobases, including mixed duplex oligonucleotides, non-nucleotide containing molecules, single stranded oligodeoxynucleotides and other gene repair molecules as described in detail below.

In some embodiments, a genetically converted yeast or non-genetically converted yeast as provided herein is derived from an oleaginous yeast. In certain preferred embodiments, a genetically converted yeast or non-genetically converted yeast as provided herein is derived from a yeast selected from the group consisting of *Cryptococcus curvatus, Yarrowia lipolytica, Rhodotorula glutinus*, and *Rhorosporidium toruloides*. In some preferred embodiments, the genetically converted yeast or non-genetically converted yeast is derived from a yeast selected from the group consisting of *Cryptococcus curvatuss, Yarrowia lipolytica*, and *Rhodotorula glutinus*. In related embodiments, the genetically converted yeast or non-genetically converted yeast is derived from a yeast selected from the group consisting of *Cryptococcus curvatus*, and *Rhodotorula glutinus*. In certain preferred embodiments, the genetically converted yeast or non-genetically converted yeast is not derived from *Yarrowia lipolytica*. In certain embodiments the genetically converted yeast or non-genetically converted yeast is a *Yarrowia lipolytica* strain selected from the group consisting of ATCC 20688, ATCC 90811, ATCC 90904, ATCC 90812, ATCC MYA-2613, and Yeastern polg.

In certain preferred embodiments, an enzyme that is modified in a genetically converted yeast as provided herein is acetyl-CoA carboxylase (or "ACCase"). In some preferred embodiments acetyl-CoA carboxylase in a genetically converted yeast is modified such that its activity and/or expression is decreased relative to the corresponding native yeast; or such that the activity and/or expression is eliminated. In other embodiments, the acetyl-CoA carboxylase may be modified so that its substrate selectivity is altered. In some preferred embodiments, the genetically converted yeast is modified such that the activity and/or expression of acetyl- CoA carboxylase is reduced relative to the corresponding native yeast but the activity is not eliminated. In some preferred embodiments, the genetically converted yeast is modified such that the activity and/or expression of acetyl-CoA carboxylase in the genetically converted yeast is reduced to about 90%; or about 80%; or about 70%; or about 60%; or about 50; or about 40%; or about 30%; or about 20%; or about 10%; or about 5% of the activity and/or expression of the corresponding native yeast. In related embodiments, the genetically converted yeast is modified such that the activity and/or expression of acetyl-CoA carboxylase in the genetically converted yeast is between about 90-95%; or about 80-90%; or about 70-80%; or about 60-70%; or about 50-60%; or about 40-50%; or about 30-40%; or about 20-30%; or about 10-20%; or about 5-10%; or about 2-5% of the activity and/or expression of the corresponding native yeast.

In certain preferred embodiments, an enzyme is modified in a genetically converted yeast as provided herein is HMG-CoA reductase. In some preferred embodiments HMG-CoA reductase in a genetically converted yeast is modified such that its activity and/or expression is increased relative to the corresponding native yeast. In other embodiments, the HMG-CoA reductase may be modified so that it substrate selectivity is altered. In certain preferred embodiments, the genetically converted yeast is modified such that the activity and/or expression of HMG-CoA reductase in the genetically converted yeast is increased to at least 1.2-fold; or 1.5-fold; or 2-fold; or 3-fold; or 4-fold; or 5-fold; or 10-fold; or 15-fold; or 20-fold; or 50-fold; or 100-fold; or 1,000-fold; or 10,000-fold; or 100,000-fold; or 1,000,000-fold higher than the activity and/or expression of the corresponding native yeast.

In certain preferred embodiments, an enzyme that is modified in a genetically converted yeast as provided herein is squalene epoxidase. In some preferred embodiments squalene epoxidase in a genetically converted yeast is modified such that its activity and/or expression is decreased relative to the corresponding native yeast; or such that the activity and/or expression is eliminated. In other embodiments, the squalene epoxidase may be modified so that its substrate selectivity is altered. In some preferred embodiments, the genetically converted yeast is modified such that the activity and/or expression of squalene epoxidase is reduced relative to the corresponding native yeast but the activity is not eliminated. In certain embodiments, the squalene epoxidase is modified to include one or more mutations or homologs of one or more mutations associated with increased sensitivity to terbinafine. In certain embodiments, the yeast is not *Saccharomyces cerevisiae* and the squalene epoxidase is modified to include the homologs of one or more of the following mutations associated with increased sensitivity to terbinafine in the *Saccharomyces cerevisiae* ERG1 gene; G30S, L37P, and R269G, (see, e.g., Turnowsky, 2005, 2007 and 2008). In certain embodiments, the yeast is *Y. lipolytica* and the squalene epoxidase is modified to include the homologs of one or more of the following mutations associated with increased sensitivity to terbinafine in the *Saccharomyces cerevisiae* ERG1 gene: G30S, L37P, and R269G (see, e.g., Turnowsky, 2005, 2007 and 2008). In some embodiments, the yeast squalene epoxidase gene is modified as described herein by synthesis and replacement of the wild-type gene or by introduction of mutations by RTDS. In some preferred embodiments, the genetically converted yeast is modified such that the activity and/or expression of squalene epoxidase in the genetically converted yeast is reduced to about 90%; or about 80%; or about 70%; or about 60%; or about 50%; or about 40%; or about 30%; or about 20%; or about 10%; or about 5%; of the activity and/or expression of the corresponding native yeast. In related embodiments, the genetically converted yeast is modified such that the activity and/or expression of squalene epoxidase in the genetically converted yeast is between about 90-95%; or about 80-90%; or about 70-80%; or about 60-70%; or about 50-60%; or about 40-50%; or about 30-40%; or about 20-30%; or about 10-20%; or about 5-10%; or about 2-5% of the activity and/or expression of the corresponding native yeast.

In certain preferred embodiments, an enzyme that is modified in a genetically converted yeast as provided herein is squalene synthase. In some preferred embodiments squalene synthase in a genetically converted yeast is modified such that its activity and/or expression is increased relative to the corresponding native yeast. In other embodiments, the squalene synthase may be modified so that it substrate selectivity is altered. In certain preferred embodiments, the genetically converted yeast is modified such that the activity and/or expression of squalene synthase in the genetically converted yeast is increased to at least 1.2-fold; or 1.5-fold; or 2-fold; or 3-fold; or 4-fold; or 5-fold; or 10-fold; or 15-fold; or 20-fold; or 50-fold; or 100-fold; or 1,000-fold; or 10,000-fold; or 100,000-fold; or 1,000,000-fold higher than the activity and/or expression of the corresponding native yeast.

In certain preferred embodiments, an enzyme that is modified in a genetically converted yeast as provided herein is ATP citrate lyase. In some embodiments, either or both subunits of ATP citrate lyase genes (for example, *Yarrowia lipolytica* ATP citrate lyase: Genoleveres YAL10D24431g and YAL10E3479g) are modified as described herein. In certain embodiments the activity of ATP citrate lyase in a modified yeast is increased by the insertion and/or heterologous expression of an animal ATP lyase gene which comprises a single subunit holoenzyme. In some preferred embodiments ATP citrate lyase in a genetically converted yeast is modified such that its activity and/or expression is increased relative to the corresponding native yeast. In certain preferred embodiments, the genetically converted yeast is modified such that the activity and/or expression of ATP citrate lyase in the genetically converted yeast is increased to at least 1.2-fold; or 1.5-fold; or 2-fold; or 3-fold; or 4-fold; or 5-fold; or 10-fold; or 10-fold; or 20-fold; or 50-fold; or 100-fold; or 1,000-fold; or 10,000-fold; or 100,000-fold; or 1,000,000-fold higher than the activity and/or expression of the corresponding native yeast.

In certain embodiments of the compositions and methods provided herein, the enzyme that is modified in a genetically converted yeast or non-genetically converted yeast is ATP citrate synthase. Preferably, its activity and/or expression is increased relative to the corresponding native yeast.

In certain preferred embodiments, an enzyme that is modified in a genetically converted yeast as provided herein is mevalonate kinase (e.g., *Y. lipolytica* mevalonate kinase (Genolevures YAL10B16038g)). In some preferred embodiments mevalonate kinase (e.g., *Y. lipolytica* mevalonate kinase (Genolevures YAL10B16038g)) in a genetically converted yeast is modified such that its activity and/or expression is increased relative to the corresponding native yeast. In certain preferred embodiments, the genetically converted yeast is modified such that the activity and/or expression of mevalonate kinase (e.g., *Y. lipolytica* mevalonate kinase (Genolevures YAL10B16038g)) in the genetically converted yeast is increased to at least 1.2-fold; or 1.5-fold; or 2-fold; or 3-fold; or 4-fold; or 5-fold; or 10-fold; or 15-fold; or 20-fold; or 50-fold; or 100-fold; or 1,000-fold; or 10,000-fold; or 100,000-fold; or 1,000,000-fold higher than the activity and/or expression of the corresponding native yeast.

In certain preferred embodiment, an enzyme that is modified in a genetically converted yeast as provided herein is glycerol kinase (e.g., *Y. lipolytica* glycerol kinase (Genolevures YAL20F00484g)). In some preferred embodiments glycerol kinase (e.g., *Y. lipolytica* glycerol kinase (Genolevures YAL10F00484g)) in a genetically converted yeast is modified such that its activity and/or expression is increased relative to the corresponding native yeast. In certain, preferred embodiments, the genetically converted yeast is modified such that the activity and/or expression of mevalonate kinase glycerol kinase (e.g., *Y. lipolytica* glycerol kinase (Genolevures YAL10F00484g)) in the genetically converted yeast is increased to at least 1.2-fold; or 1.5-fold; or 2-fold, or 3-fold; or 4-fold; or 5-fold; or 10-fold: or 15 fold; or 20-fold; or 50-fold; or 100-fold; or 1,000-fold; or 10,000-fold; or 100,000-fold; or 1,000,000-fold higher than the activity and/or expression of the corresponding native yeast.

In certain embodiments of the compositions and methods provided herein, the enzyme that is modified in a genetically converted yeast, or non-genetically converted yeast is 5-aminolevulinate synthase (e.g., encoded by *Saccharomyces cerevisiae* HEM1 gene). Preferably, its activity end/or expression is increased relative to the corresponding native yeast.

In certain preferred embodiments of the above aspects, the genetically converted yeast is a genetically converted yeast; in other preferred embodiments, the genetically converted yeast is a transgenic yeast. Further embodiments are a yeast that includes both transgenic and genetic alterations.

In certain aspects and embodiments, provided are compositions that include a yeast (for example a genetically converted yeast such as disclosed herein or a non-genetically converted yeast) wherein at least 10% of the total lipid content is squalene; or at least 20% of the total lipid cement is squalene; or at least 25% of the total lipid content is squalene; or at least 28% of the total lipid content is squalene; or at least 30% of the a set lipid content is squalene; or at least 32% of the total lipid content is squalene; or at least 35% of the total lipid content is squalene; or at least 37% of the total lipid content is squalene; or at least 38% of the total lipid content is squalene; or at least 40% of the total lipid content is squalene; or at least 42% of the total lipid content is squalene; or at least 45% of the total lipid content is squalene; or at least 47%, of the total lipid content is squalene; or at least 50% of the total lipid content is squalene; or at least 52% of the total lipid content is squalene; or at least 55% of the total lipid content is squalene; or at least 57% of the total lipid content is squalene; or at least 60% or more of the total lipid content is squalene.

In still further embodiment of various aspects disclosed herein, there are provided isoprenoids, such as squalene, extracted from any of the above or below described genetically converted, transgenic genetically converted or non-genetically converted yeast.

The phrase "genetically converted yeast" or "genetically altered yeast" as used herein refers to a yeast having one or more genetic modifications, such as transgenes and/or modified enzymes winch contain one or more designed mutation(s). Such designed mutations may result in a modified enzyme having an activity that is different from the native enzyme. Such differences can include differences in substrate specificity or level of activity. As used herein, a "transgenic yeast" is one type of a "genetically converted yeast".

The term "native yeast" as used herein refers to a yeast that is not genetically converted (i.e., transgenic or genetically altered). Native yeasts include wild type yeasts as well as yeasts that have been selectively bred to attain particular characteristics.

The phrase "transgenic yeast" refers to a yeast having a gene from another yeast species or non-yeast species. Such a gene may be referred to as a "transgene."

As used herein the term "target gene" refers to the encoding the enzyme to be modified.

The phrase "oleaginous yeast" refers in a yeast that contains at least about 20% cell dry weight (cdw) lipid extractable from the organism. The capacity to accumulate levels of lipid at least about 20% cdw is not confined to a particular genus; greater than about 20% cdw lipid has been reported in *Lipomyces lipofer, L. starkeyi, L. tetrasporus, Candida lipolytica, C. diddensiae, C. paralipolytica, C. curvata, Cryptococcus albidus, Cryptococcus laurentii, Geotriclum candidum, Rhodotoroula graminus, Trichosporon pullulans, Rhodosporidium toruloides, Rhodotorula glutinus, Rhodotorula gracilis*, and *Yarrowia lipolytica*. See, e.g., Tatsumi, et al. U.S. Pat. No. 4,032,405, and Rattray, *Microbiol Lipids. Vol.* 1 (1998).

The term "about" as used herein means in quantitative terms plus or minus 10%. For example, "about 3%" would encompass 2.7-3.3% and "about 10%" would encompass 9-11%.

Unless otherwise indicated, any percentages stated herein are percent by weight.

Other features and advantages of the invention will be apparent from the following description of the preferred embodiments and from the claims.

DETAILED DESCRIPTION OF THE INVENTION

Types of Yeast

The compositions and methods as disclosed herein can be based on any of a number of yeast species or strains. In certain embodiments, the yeast is an oleaginous yeast. For example the yeast may be *Cryptococcus curvatus* (for example ATCC 20508), *Yarrowia lipolytica* (for example ATCC 20688 or ATCC 90811), *Rhodotorula glutinus* (for example ATCC 10788 or ATCC 204091), and *Rhorosporidium toruloides*. The inventors have discovered that, relative to certain other yeast (such as *Yarrowia lipolytica*), *Cryptococcus curvatus* and *Rhodotorula glutinis* grow to very high cell densities on a wide variety of substrates, and produce large amount of total lipid under many culture conditions. Accordingly, in certain embodiments *Cryptococcus curvatus* and *Rhodotorula glutinis* may be particularly advantageous for the compositions and methods as disclosed herein. There are many genetic tools (for example, transformation protocols, selectable markers) that are well developed and specific for *Yarrowia lipolytica*; as such in some embodiments *Yarrowia lipolytica* may be particularly advantageous for the compositions and methods as disclosed herein. In certain embodiments of the compositions and methods disclosed herein the yeast (either genetically converted or non-genetically converted) may be a *Yarrowia lipolytica* strain such as ATCC 20688, ATCC 90811, ATCC 90904, ATCC 90812, ATCC MYA-2613, or Yeastern polg.

Gene Repair Oligonucleobases

The invention can be practiced with "gene repair oligonucleobases" having the conformations and chemistries as described in detail below. The "gene repair oligonucleobases" of the invention include mixed duplex oligonucleotides, non-nucleotide containing molecules, single stranded oligodeoxynucleotides and other gene repair molecules described in the below noted patents and patent publications. The "gene repair oligonucleobases" of the invention have also been described in published scientific and patent literature using other names including "recombinagenic oligonucleobases;" "RNA/DNA chimeric oligonucleotides;" "chimeric oligonucleotides;" "mixed duplex oligonucleotides (MDONs);" "RNA DNA oligonucleotides (RDOs);" "gene targeting oligonucleotides;" "genoplasts;" "single stranded modified oligonucleotides;" "Single stranded oligodeoxynucleotide mutational vectors;" "duplex mutational vectors;" and "heteroduplex mutational vectors."

Oligonucleobases having the conformations and chemistries described in U.S. Pat. No. 5,565,350 by Kmiec (Kmiec I) and U.S. Pat. No. 5,731,181 by Kmiec (Kmiec II), hereby incorporated by reference, are suitable for use as "gene repair oligonucleobases" of the invention. The gene repair oligonucleobases in Kmiec I and/or Kmiec II contain two complementary strands, one of which contains at least one segment of RNA-type nucleotides (an "RNA segment") that are base paired to DNA-type nucleotides of the other strand.

Kmiec II discloses that purine and pyrimidine base-containing non-nucleotides can be substituted for nucleotides. Additional gene repair molecules that can be used for the present invention are described in U.S. Pat. Nos. 5,736,325; 5,871,984; 5,760,012; 5,888,983; 5,795,972; 5,780,296; 5,945,339; 6,004,804; and 6,010,907 and in International Patent No. PCT/US00/23457; and in International Patent Publication Nos. WO 98/49350; WO 99/07865; WO 99/58723; WO 99/58702; and WO 99/40789, which are each hereby incorporated in their entirety.

In one embodiment, the gene repair oligonucleobase is a mixed duplex oligonucleotide in which the RNA-type nucleotides of the mixed duplex oligonucleotide are made RNase resistant by replacing the 2'-hydroxyl with a fluoro, chloro or bromo functionally or by placing a substituent on the 2'-O. Suitable substituents include the substituents taught by the Kmiec II. Alternative substituents include the substituents taught by U.S. Pat. No. 5,334,711 (Sproat) and the substitutents taught by patent publications EP 629 387 and EP 679 657 (collectively, the Martin Applications), which are hereby incorporated by reference. As used herein, a 2'-fluoro, chloro or bromo derivative of a ribonucleotide or a ribonucleotide having a 2'-OH Substituted with a substituent described in the Martin Applications or Sproat is termed a "2'-Substituted Ribonucleotide." As used herein the term "RNA-type nucleotide" means a 2'-hydroxyl or 2'-Substituted Nucleotide that is linked to other nucleotides of a mixed duplex oligonucleotide by an unsubstituted phosphodiester linkage or any of the non-natural linkages taught by Kmiec I or Kmiec II. As used herein the term "deoxyribo-type nucleotide" means a nucleotide having a 2'-H, which can be linked to other nucleotides of a gene repair oligonucleobase by an unsubstituted phosphodiester linkage or any of the non-natural linkages taught by Kmiec I or Kmiec II.

In a particular embodiment of the present invention, the gene repair oligonucleobase is a mixed duplex oligonucleotide that is linked solely by unsubstituted phosphodiester bonds. In alternative embodiments, the linkage is by substituted phosphodiesters, phosphodiester derivatives and non-phosphorus-based linkages as taught by Kmiec II. In yet another embodiment, each RNA-type nucleotide in the mixed duplex oligonucleotide is a 2'-Substituted Nucleotide. Particular preferred embodiments of 2'-Substituted Ribonucleotides are 2'-fluoro, 2'-methoxy, 2'-propyloxy, 2'-allyloxy, 2'-hydroxylethyloxy, 2'-methoxyethyloxy, 2'-fluoropropyloxy and 2'-trifluoropropyloxy substituted ribonucleotides. More preferred embodiments of 2'-Substituted Ribonucleotides are 2'-fluoro, 2'-methoxy, 2'-methoxyethyloxy, and 2'-allyloxy substituted nucleotides. In another embodiment the mixed duplex oligonucleotide is linked by unsubstituted phosphodiester bonds.

Although mixed duplex oligonucleotides having only a single type of 2'-substituted RNA-type nucleotide are more conveniently synthesized, the methods of the invention can be practiced with mixed duplex oligonucleotides having two or more types of RNA-type nucleotides. The function of an RNA segment may not be affected by an interruption caused by the introduction of a deoxynucleotide between two RNA-type trinucleotides, accordingly, the term RNA segment encompasses such as "interrupted RNA segment." An uninterrupted RNA segment is termed a contiguous RNA segment. In an alternative embodiment an RNA segment can contain alternating RNase-resistant and unsubstituted 2'-OH nucleotides. The mixed duplex oligonucleotides preferably have fewer than 100 nucleotides and more preferably fewer than 85 nucleotides, but more than 50 nucleotides. The first and second strands are Watson-Crick base paired. In one embodiment the strands of the mixed duplex oligonucleotide are covalently bonded by a linker, such as a single stranded hexa, penta or tetranucleotide so that the first and second strands are segments of a single oligonucleotide chain having a single 3' and a single 5' end. The 3' and 5' ends can be protected by the addition of a "hairpin cap" whereby the 3' and 5' terminal nucleotides are Watson-Crick paired to adjacent nucleotides. A second hairpin cap can, additionally, be placed at the junction between the first and second strands distant horn the 3' and 5' ends, so that the Watson-Crick pairing between the first and second strands is stabilized.

The first and second strands contain two regions that are homologous with two fragments of the target gene, i.e., have the same sequence as the target gene. A homologous region contains the nucleotides of an RNA segment and may contain one or more DNA-type nucleotides of connecting DNA segment and may also contain DNA-type nucleotides that are not within the intervening DNA segment. The two regions of homology are separated by, and each is adjacent to, a region having a sequence that differs from the sequence of the target gene, termed a "heterologous region." The heterologous region can contain one, two or three mismatched nucleotides. The mismatched nucleotides can be contiguous or alternatively can be separated by one or two nucleotides that are homologous with the target gene. Alternatively, the heterologous region can also contain an insertion or one, two, three or of five or fewer nucleotides. Alternatively, the sequence of the mixed duplex oligonucleotide may differ from the sequence of the target gene only by the deletion of one, two, three, or five or fewer nucleotides from the mixed duplex oligonucleotide. The length and position of the heterologous region is, in this case, deemed to be the length of the deletion, even though no nucleotides of the mixed duplex oligonucleotide are within the heterologous region. The distance between the fragments of the target gene that are complementary to the two homologous regions is identically the length of the heterologous region when a substitution or substitutions is intended. When the heterologous region contains an insertion, the homologous regions are thereby separated in the mixed duplex oligonucleotide farther than their complementary homologous fragments are in the gene, and the converse is applicable when the heterologous region encodes a deletion.

The RNA segments of the mixed duplex oligonucleotides are each a part of a homologous region, i.e., a region that is identical in sequence to a fragment of the target gene, which segments together preferably contain at least 13 RNA-type nucleotides and preferably from 16 to 25 RNA-type nucleotides or yet more preferably 18-22 RNA-type nucleotides or most preferably 20 nucleotides. In one embodiment, RNA segments of the homology regions are separated by and adjacent to, i.e., "connected by" an intervening DNA segment. In one embodiment, each nucleotide of the heterologous region is a nucleotide of the intervening DNA segment. An intervening DNA segment that contains the heterologous region of a mixed duplex oligonucleotide is termed a "mutator segment."

In another embodiment of the present invention, the gene repair oligonucleobase is a single stranded oligodeoxynucleotide mutational vector (SSOMV), which is disclosed in International Patent Application PCT/US00/23457, U.S. Pat. Nos. 6,271,360, 6,479,292, and 7,060,500 which is incorporated by reference in its entirety. The sequence of the SSOMV is based on the same principles as the mutational vectors described in U.S. Pat. Nos. 5,756,325; 5,871,984; 5,760,012; 5,888,983; 5,795,972; 5,780,296; 5,945,339; 6,004,804; and 6,010,907 and in International Publication Nos. WO 98/49350; WO 99/07865; WO 99/58723; WO 99/58702; and WO 99/40749. The sequence of the SSOMV contains two regions that are homologous with the target sequence separated by a region that contains the desired genetic alteration termed the mutator region. The mutator region can have a sequence that is the same length as the sequence that separates the homologous regions in the target sequence, but having a different sequence. Such a mutator region can cause a substitution. Alternatively, the homologous regions in the SSOMV can be contiguous to each other, while the regions in the target gene having the same sequence are separated by one, two or more nucleotides. Such a SSOMV causes a deletion from the target gene of the nucleotides that are absent from the SSOMV. Lastly, the sequence of the target gene that is identical to the homologous regions may be adjacent in the target gene but separated by one two or more nucleotides in the sequence of the SSOMV. Such an SSOMV causes an insertion in the sequence of target gene.

The nucleotides of the SSOMV are deoxyribonucleotides that are linked by unmodified phosphodiester bonds except that the 3' terminal and/or 5' terminal internucleotide linkage or alternatively the two 3' terminal and/or 5' terminal internucleotide linkages can be a phosphorothioate or phosphoamidate. As used herein an internucleotide linkage is the linkage between nucleotides of the SSOMV and does not include the linkage between the 3' end nucleotide or 5' end nucleotide and a blocking substituent, see supra. In a specific embodiment the length of the SSOMV is between 21 and 55 deoxynucleotides and the lengths of the homology regions are accordingly, a total length of at least 20 deoxynucleotides and at least two homology regions should each have lengths of at least 8 deoxynucleotides.

The SSOMV can be designed to be complementary to either the coding or the non-coding strand of the target gene. When the desired mutation is a substitution of a single base, it is preferred that both the mutator nucleotide be a pyrimidine. To the extent that is consistent with achieving the desired functional result it is preferred that both the mutator nucleotide and the targeted nucleotide in the complementary strand be pyrimidines. Particularly preferred are SSOMV that encode transversion mutations, i.e., a C or T mutator nucleotide is mismatched, respectively, with a C or T nucleotide in the complementary strand.

In addition to the oligodeoxynucleotide the SSOMV can contain a 5' blocking substituent that is attached to the 5' terminal carbons through a linker. The chemistry of the linker is not critical other than its length, which should preferably be at least 6 atoms long and that the linker should be flexible. A variety of non-toxic substituents such as biotin, cholesterol or other steroids or a non-intercalating cationic fluorescent dye can be used. Particularly preferred as reagents to make SSOMV are the reagents sold as Cy3™ and Cy5™ by Glen Research, Sterling Va., which are blocked phosphoroamidites that upon incorporation into an oligonucleotide yield 3,3,3',3'-tetramethyl N,N'-isopropyl substituted indomonocarbocyanine and indodicarbocyanine dyes, respectively. Cy3 is the most preferred. When the indocarbocyamine is N-oxyalkyl substituted, it can be conveniently linked to the 5' terminal of the oligodeoxynucleotide through as a phosphodiester with a 5' terminal phosphate. The chemistry of the dye linker between the dye and the oligodeoxynucleotide is not critical and is chosen for synthetic convenience. When the commercially available Cy3 phosphoramidite is used as directed the resulting 5' modification consists of a blocking substituent and linker together which are a N-hydroxypropyl, N'-phosphatidylpropyl 3,3,3',3'-tetramethyl indomonocarbocyanine.

In one preferred embodiment the indocarbocyamine dye is tetra substituted at the 3 and 3' positions of the indole rings. Without limitations as to theory these substitutions prevent the dye from being an intercalating dye. The identity of the substituents as these positions are not critical. The SSOMV can in addition have a 3' blocking substitutent. Again the chemistry of the 3' blocking substituent is not critical.

Heterologous Expression

In certain embodiments, heterologous expression is used to express foreign genes or extra copies of endogenous genes in yeast (for example, *Yarrowia lipolytica*). Heterologous expression in yeast can be performed using methods well known in the art. Expression of foreign genes or extra copies of endogenous genes in yeast using heterologous expression may involve use of a vector that includes (a) promoter sequences for transcriptional initiation, (b) terminator sequences for termination of transcription, and (c) a selectable marker. Heterologous expression and expression vectors may be as described, for example, in Madzak, C., Gaillardin, C., and Beckerich, J-M., 2004 Heterologous Protein Expression and Secretion in the Non-Conventional Yeast *Yarrowia lipolytica*: a review, Journal of Biotechnology 109:63-81. In certain embodiments of the compositions and methods herein, the vector is pYLEX1 (Yeastern). A non-limiting list of selectable marker genes that may be used includes ura3, lys5, trp1, leu2, ade1, *E. coli* hph encoding hygromycin resistance, and SUC2 from *Saccharomyces cerevisiae*. A non-limiting list of promoters that may be used includes pLEU2, pXPR2, pPOX2, pPOT1, pICL1, pG3P, pMTP, pTEF, and pRPS7. In certain embodiments, the promoter is the hp4d promoter, which is a strong, constitutive hybrid promoter (U.S. Pat. No. 6,083,717 issued Jul. 4, 2000). A non-limiting list of terminator sequences that may be used includes XPR2t, LIP2t, and PHO5t.

In certain embodiments, one or more of *Yarrowia lipolytica* LYS1 (Genolevures YAL10B15444g), TRP1 and (Genolevures YAL10B07667g), and ADE1 (Genolevures YAL10E33033g) genes are used as selectable markers. In certain embodiments on or more of *Yarrowia lipolytica* URA3 (GenBank: U40564.1) or LEU2 (Genoluveres YAL10C00407) genes are used as selectable markers.

In certain embodiments an integrative expression vector includes one or more promoters and/or terminator sequences selected from the group consisting of *Yarrowia lipolytica* glycolytic pathway genes, alkane or glycerol utilization genes, XPR2, ACC1, HMG1, ERG1, and ERG9.

In certain embodiments of one or both subunits of *Yarrowia lipolytica* ATP citrate lyase (Genoleveres YAL10D24434g and YAL10E34793g) in *Yarrowia lipolytica* are overexpressed.

Modified Enzymes

A modified or mutated enzyme of the present disclosure can be modified or mutated by base pair changes, insertions, substitutions, and the like.

The genes encoding-enzymes involved in the fatty acid biosynthesis pathway and isoprenoid biosynthesis pathway are the preferred targets for mutation. In some embodiments the target gene encodes an acyl CoA carboxylase. In other embodiments the target gene encodes an HMG-CoA reductase. In other embodiments the target gene encodes a squalene epoxidase. In other embodiments the target gene encodes a squalene synthase. In certain embodiments the target gene encodes ATP citrate lyase. Mutations can be designed that reduce or eliminate the activity of an enzyme, enhance the activity of an enzyme, or that alter the activity of the enzyme (e.g., change the substrate selectivity).

In wild-type oleaginous yeast, acetyl-CoA is extensively channeled into fatty acid biosynthesis via acetyl-CoA carboxylase (ACCase). Thus in order to increase the amount of acetyl-CoA available for squalene synthesis, it is desirable to reduce the enzymatic expression or specific activity of ACCase. An exemplary gene sequence for ACCase is the ACC1 gene in *Saccharomyces cerevisiae* as shown in accession number Z71631. Accordingly in certain embodiments reduced intracellular activities of ACCase, the enzyme at the branch point between mevalonate biosynthesis and triglyceride biosynthesis will decrease the amount of acetyl-CoA partitioned for oil synthesis, thereby increasing its availability to the isoprene pathway.

HMG-CoA reductase activity is the rate-limiting enzyme for isoprene biosynthesis. Exemplary gene sequences for HMG-CoA reductase include the HMG1 and HMG1 genes in *Saccharomyces cerevisiae* as shown in accession numbers NC_001145 and NC_001144, respectfully. Accordingly, in certain embodiments HMG-CoA reductase activity will be increased by muddying the HMGR gene to increase transcription, stabilize the resultant protein, and/or reduce product feedback inhibition.

Decreasing are activity and/or increasing HMG-CoA reductase activity in a yeast can create a core isoprenoid production organism capable of producing a number of related isoprenoid products by the manipulation of subsequent enzymes in the pathway.

Squalene epoxidase catalyzes the first committed step of sterol biosynthesis. An exemplary gene sequence for Squalene epoxidase is the ERG1 gene in *Saccharomyces cerevisiae* as shown in accession number NC_001139. Accordingly, in certain embodiments squalene epoxidase activity, sensitivity to inhibitors and/or expression will be attenuated in a yeast, for example by catalytically important residues in the enzyme's amino acid sequence.

Squalene synthase catalyzes the synthesis of squalene by condensing two c15 isoprene precursors (farnesyl diphosphate (FPP)). An exemplary gene sequence for squalene synthase is the ERG9 gene in *Saccharomyces cerevisiae* as shown in accession number NC_001140. Accordingly, in certain embodiments squalene synthase activity and/or expression will be increased in a yeast.

ATP citrate lyase (E.C. 4.1.3.8) catalytically cleaves citrate to produce acetyl CoA and oxaloacetate. Acetyl CoA can be used by ACCase for fatty acid biosynthesis or by acetyl CoA acetyl transferase for the production of isoprenes and derivatives such as squalene.

Mevalonate kinase is the first enzyme after HMG-CoA Reductase in the mevalonate pathway, and catalyzes the conversion of Mevalonate to Mevalonate-5-phosphate. Accordingly, in certain embodiments mevalonate kinase activity and/or expression levels will be increased in yeast, for example, by changing catalytically important residues in the enzyme's amino acid sequence or increasing its gene dosage or transcript levels.

Glycerol kinase catalyzes the transfer of a phosphate from ATP to glycerol to form glycerol phosphate. Accordingly, in certain embodiments glycerol kinase activity and/or expression levels will be increased in yeast, for example, by changing catalytically important residues in the enzyme's amino acid sequence or increasing its gene dosage or transcript levels.

The result of the metabolic changes in certain embodiments will be to channel carbon from acetyl-CoA to squalene, and attenuate major competitive pathways for this carbon stream, resulting in a significant increase of squalene produced.

Delivery of Gene Repair Oligonucleobases into Yeast cells

Any commonly known method can be used in the methods of the present invention to transform a yeast cell with a gene repair oligonucleobase. Exemplary methods include the use of electroporation, LiOAc, biolistics, spheroplasting, and/or *Agrobacterium* (see, for example, McClelland, C. M., Chang, Y. C., and Kwon-Chang, K. J. (2005) Fungal Genetics and Biology 42:904-913).

In certain embodiments, a gene repair oligonucleobase is introduced into a yeast cell by electroporation. In some embodiments a gene repair oligonucleobase is introduced into a yeast cell that has bean chemically treated with PEG (3350 or 4000 mw) and/or Lithium Acetate by electroporation. In certain embodiments a gene repair oligonucleobase is introduced into a yeast cell using PEG (3350 or 4000 mw) and/or Lithium Acetate.

Specific conditions for using microcarriers in the methods of the present invention are described in International Publication WO 99/07865, U.S. Ser. No. 09/129,298. For example, ice cold microcarriers (60 mg/mL), mixed duplex oligonucleotides (60 mg/mL). 2.5 M $CaCl_2$ and 0.1 M spermidine are added in that order; the mixture gently agitated, e.g., by vortexing, for 10 minutes and let stand at room temperature for 10 minutes; whereupon the microcarriers are diluted in 5 volumes of ethanol, centrifuged and resuspended in 100% ethanol. Exemplary concentrations of the components in the adhering solution include 8-10 μg/μL microcarriers, 14-17 μg/μL mixed duplex oligonucleotide, 1.1-1.4 M $CaCl_2$ and 18-22 mM spermidine. In one example, the component concentrations are 8 μg/μL microcarriers, 16.5 μg/μL mixed duplex oligonucleotide, 1.3 M $CaCl_2$ and 21 mM spermidine.

In some embodiments, gene repair oligonucleobases can be delivered to the yeast cell by electroporation, according to techniques well known to those skilled in the art. (See, e.g. Becker, D. M., and Guarente, L. High Efficiency Transformation of Yeast by Electroporation. Methods in Enzymology, vol. 194, section [12] pp. 182-186, 1991, Elsevier Academic Press, London.

Selection of Yeast Having the Desired Modified Enzyme

Yeast expressing the modified enzyme can be identified through any of a number of means. In one method, a co-conversion strategy using gene repair oligonucleobases (GRONs) to target both a selectable conversion (i.e., a marker) and a non-selectable conversion (e.g., a target gene of interest) in the same experiment. In this way, the cells to which GRONs were not delivered or were unable to transmit the conversions specified by the GRON would be eliminated. Since delivery of GRONs targeting unrelated genes is not expected to be selective, at some frequency, a colony with a successfully selected conversion would also be expected to have a conversion in one of the other targeted genes. Conversion events would be resolved by single nucleotide polymorphism (SNP) analysis.

Thus, genomic DNA is extracted from yeast and screening of the individual DNA samples using a SNP detection technology, e.g., allele-specific Polymerase Chain Reaction (ASPCR), for each target. To independently confirm the sequence change in positive yeast, the appropriate region of the target gene may be PCR amplified and the resulting amplicon either sequenced directly or cloned and multiple inserts sequenced.

Alternatively, the incorporation of the mutation into the gene of interest can be identified by any of a number of molecular biology techniques designed to detect single nucleotide mutations in extracted nucleic acid (e.g., amplification methods such as PCR and single nucleotide primer extension analysis). Larger mutations can be detected by amplification and sequencing of the region of the target gene to be mutated.

Alternatively, yeast or yeast cells containing the modified enzyme can be identified by, for example, analysis of the composition of isoprenoids produced by the yeast. Thus, the yeast can be grown and oils extracted and analyzed using methods known in the art (e.g., gas chromatography or HPLC).

EXAMPLES

Example 1

*Cryptococcus curvatus* and *Rhodotorula glutinis* Transformation Systems

To create a *Cryptococcus curvatus* (ATCC strain 20508) and *Rhodotorula glutinis* (ATCC strains 10788 and 20491) transformation system, a KANMX expression cassette (promoter-gene-terminator) which confers kanamycin resistance to *S. cerevisiae* is used as a selectable marker to convert the strains from kanamycin sensitivity to resistance (See e.g., Baudin, A., et al. (1993) Nucleic Acids Research (21) 3329-3330). The strains are transformed with the expression cassette alone, as well as KANMX ligated to restriction fragments of a plasmid reported in *R. glutinus* (See e.g. Oloke, J. K., and Glick, B. R. (2006) African Journal of Biotechnology 5(4):327-332) containing DNA origins of replication. DNA is introduced into *C. curvatus* and *R. glutinis* by electroporation, LiOAc, biolistics, spheroplasting, and/or *Agrobacterium* (McClelland, C. M., Chang, Y. C., and Kwon-Chung, K. J. (2005) Fungal Genetics and Biology 42:904-913).

Example 2

Selectable Markers

To generate uracil auxotrophic mutants in *Cryptococcus curvatus* and *Rhodotorula glutinis*, cells were grown in minimal media containing anti-metabolite 5-fluoroorotic acid to select for resistant mutants with lesions in the ura3 and ura5 genes. 33 stable 5-FOA$^R$ colonies of *Cryptococcus curvatus* and 20 stable 5-FOA$^R$ colonies of *Rhodotorula glutinis* were banked. Wild type URA3 genes from both *Cryptococcus curvatus* and *Rhodotorula glutinis* are cloned and the mutant ura3 genes in the 5-FOA$^R$ isolates are sequenced.

Other auxotrophic markers are cloned by functional complementation in *Saccharomyces cerevixiae* (See Ho, Y. R., and Chang, M. C. (1988) Chinese Journal of Microbiology and Immunology 21(1):1-8). Genomic and/or cDNA libraries are constructed from *Cryptococcus curvatus* and *Rhodotorula glutinis* for ligation into a uracil-selectable *Saccharomyces* expression vector for transformation into strain YPH500 (MATa ura3-52 lys2-801 ade2-101 trp1-Δ63 his3-Δ200 leu2-Δ1) to select for lysine, adenine, tryptophan, histidine, and leucine prototrophs. From these prototrophs, the corresponding genes for LYS2, ADE2, TRP1, HIS3, and LEU2 are sequenced from the genomic or cDNA insert.

Example 2

Gene Manipulation in Yeast Using RTDS Technology

The alleles of the leu2, lys5 and ura3 genes from *Yarrowia lipolytica* strain ATCC 90811 (leu2-35 lys5-12 ura3-18 XPR2B) were cloned by PCR and their sequences compared to the wild type alleles to identity differences.

For ura3, differences were found at positions 1365 (A→G mutation, resulting in a silent change of AAA→AAG coding for lysine), 1503 (AAGAA extra sequences in ATCC 90811 which results in a frame change, but which comes back in frame at 1511 resulting in 7 additional amino acids, after which the sequence continues as the YL URA3 in GenBank), 1511 (extra T In ATCC 90811), and 1978 (C→T mutation, leading to a stop mutation truncating the protein 24 amino acids short of the carboxy terminus). A GRON oligonucleotide was designed to restore prototroghy by converting STOP(TGA)→R (CGA) to yield 264R based on YlUra3-YlUra40564 amino acid numbering. The GRONs used are YlUra31264/C/5/40/5'Cy3/3'idC, which has the sequence VCGAGGTCTGTACGGCCAGAACCGA-GATCCTATTGAGGAGGH, and YlUra32164/NC/40/5═Cy3/3'idC, which has the same sequence VCCTCCT-CAATAGGATCTCGGTTCTGGCCGTACAGACCTCGH, where V=CY3; H=3'DMT dC CPG. 10, 30, and 50 µg of each of the GRONs were transformed into *Yarrowia Lipolytica* strain ATCC 90811 using a Lithium acetate-based method, and plated onto ura– 2% Glucose. A total of 82 ura+ colonies were obtained with the GRON designed using the coding strand and 6 colonies with the GRON designed using the non-coding strand, demonstrating the strand bias common in transforming with gap-repair oligonucleotides. Sequencing of 18 of the coding-strand transformants demonstrated the intended change in 17 of the clones.

For LEU2 differences were found at positions 1710 (extra C absent leading to a frame shift and premature protein termination); 1896 (extra T); 2036 (T→A mutation, located after the stop codon); 2177 (extra T in missing, located alter stop codon).

For LEU2 differences were found at positions 1092 (G→A TCG→TCA, a conservative substitution (Serine)); 1278 (G→A CAG→CAA, a conservative substitution (Glutamine)); 1279 (G→A GGT→ATT, changing V→I).

Accordingly, the mutations can be used for various purposes, for example to convert prototrophic yeast to become auxotrophic and vice versa.

A similar strategy for demonstrating the effectiveness of RTDS technology in *Cryptococcus curvatus* and *Rhodotorula glutinis* is performed as described for *Yarrowia lipolytica* in which ura3 mutations are corrected to restore prototrophy.

In certain embodiments, the effectiveness of RTDS in *Y. lipolytica* may be demonstrated by integrating a mutated version of the *E. coli* end hygromycin gene into as genome. This version of the gene, winch harbors a point mutation at G34T, encodes an E12STOP change such that the natural hygromycin sensitivity of *Y. lipolytica* is not affected. Transformation with a GRON correcting this mutation will confer resistance of the *Y. lipolytica* strain, for example, up to 1000 ug/ml of hygromycin. Double mutations in the hygromycin resistance (HGH) gene are also constructed, comprising of G34T A37T (E12STOP K13STOP) which may be corrected by a single GRON and G34T149G (E12STOP Y46STOP) which may be corrected by 2 GRONS.

To testing GRON activity in *Yarrowia*, the natural sensitivity of wild-type *Yarrowia lipolytica* to the aminoglycoside antibiotic hygromycin B was used. Hygromycin B (hmB) is an aminocyclitol antibiotic produced by *Streptomyces hygroscopicus* which inhibits protein synthesis in both procaryotes and eucaryotes by interfering with ribosomal translocation and with aminoacyltRNA recognition. Resistance can be conferred by introduction by the hph gene (also known as aph(4)) from *E. coli* (GENBANK V01499) which encodes an aminocyclitol phosphotransferase that inactivates hygromycin B by covalent addition of a phosphate group to the 4-position of the cyclitol ring. *Yarrowia lipolytica* strain Polg (Mat a ura3-302::URA3 leu2-270 xpr2-322 axp-2 from Yeastern) was transformed with the *E. coli* hph gene containing either a single (E12stop from G34T) or double mutation E12stopK13stop (G34T.A37T) mutations cloned into vector pyLEX1-2u-ura3-13, putting the gene under control of the hpd4 promoter and XPR2 terminator. The linearized vector was integrated into the genome upon selection for restoration of prototrophy conferred by the LEU2 marker. The resultant strains harbor disabled versions of the hygromycin phosphotransferase gene (hence hygromycin sensitive), and were converted with the following GRONs restoring either G34T or G34T.A37T to wild type (hygromycin resistant).

```
GRONs for restoring E12stop to wild thing (T34G)
HPH2/C/42/5'Cy3/3'idC
5'Cy3-GAACTCACCGCGACGTCTGTCGAGAAGTTTCTGATCGAAAAG-3'idC
HPH2/NC/42/5'Cy3/3'idC
5'Cy3-HCTTTTCGATCAGAAACTTCTCGACAGACGTCGCGGTGAGTTC-3'idC GRONs for restoring E12stopK13stop to wild thing (T34G T37A)
HPH3/C/43/5'Cy3/3'idC
5'Cy3-CTCACCGCGACGTCTGTCGAGAAGTTTCTGATCGAAAAGTTCG-3'idC
HPH3/NC/43/5'Cy3/3'idC
5'Cy3-CGAACTTTTCGATCAGAAACTTCTCGACAGACGTCGCGGTGAG-3'idC
```

30 μg of the indicated GRON was used to convert the single- or double-hph mutant strain in replicate (×6), pooled, and an aliquot plated onto YEPD plates containing 100-1000 μg/ml hygromycin to optimize the signal-to-noise ratio. With both strains, significant numbers of putatively converted colonies were obtained at any given hygromycin concentration above the 'No DNA' control, with a strong bias toward the non-coding GRON strand in both cases. Taken together, these results suggest GRON conversion of the hygromycin phosphotransferase gene target in *Yarrowia lipolytica*, and further that conversion of two mutations (T34G T37A) can be accomplished using a single GRON. DNA sequencing is performed to confirm restoration of the wild-type genotype.

| Strain | DNA | Colonies on 100 μg/ml Hygromycin | Colonies on 200 μg/ml Hygromycin | Colonies on 400 μg/ml Hygromycin | Colonies on 600 μg/ml Hygromycin | Colonies on 800 μg/ml Hygromycin | Colonies on 1000 μg/ml Hygromycin |
|---|---|---|---|---|---|---|---|
| E12stop | No DNA | 0 | 0 | 1 | 1 | 0 | 0 |
| E12stop | 30 μg coding strand | 0 | 1 | 6 | 1 | 1 | 0 |
| E12stop | 30 μg non-coding strand | 20 | 21 | 21 | 12 | 10 | 8 |

-continued

| Strain | DNA | Colonies on 100 μg/ml Hygromycin | Colonies on 200 μg/ml Hygromycin | Colonies on 400 μg/ml Hygromycin | Colonies on 600 μg/ml Hygromycin | Colonies on 800 μg/ml Hygromycin | Colonies on 1000 μg/ml Hygromycin |
|---|---|---|---|---|---|---|---|
| E12stopK13stop | No DNA | 0 | 0 | 4 | 1 | 0 | 0 |
| E12stopK13stop | 30 μg coding strand | 2 | 2 | 1 | 2 | 0 | 2 |
| E12stopK13stop | 30 μg non-coding strand | 5 | 3 | 5 | 7 | 8 | 8 |

Example 3

Cloning of Target Genes

The sequences for ACCase, HMGR, squalene synthase and squalene epoxidase, available in the NCBI database from *Saccharomyces* and other yeasts, are used as a source of PCR primers and the corresponding genes are cloned from *Cryptococcus curvatus* and *Rhodotorula glutinis* along with their corresponding regulatory regions (promoters, terminators). To identify 'up' 'down' promoter mutations that increase or decrease transcription, respectively, the promoters for these four genes are cloned with a relatively error-prone DNA polymerase to generate point mutations in the promoters, and these fragments are cloned into plasmids fused with Green Fluorescent Protein (GFP) or beta-galactosidase reporter genes for testing in vitro in *S. cerevisiae* or *E. coli*. Promoter "up" mutations are reintroduced into the HMGR and squalene synthase genomic sequences by RTDS, while "down" promoter mutations are being made in the genomic ACCase and squalene epoxidase sequences. The promoters from essential genes (e.g., GAPDH, actin) in *R. glutinis* and *C. curvatus* are cloned for use in heterologous gene expression. Primers for PCR cloning are designing from homology to these genes in *S. cerevisiae*.

Example 4

Manipulation of Target Genes for Increased Squalene Production

ACCase.

The number of copies of the ACCase gene is determined in *R. glutinis* and *C. curvatus* and other yeasts. RTDS is utilized to reduce ACCase expression by introducing stop codons immediately after the translational start site in any extra copies.

Squalene Epoxidase.

Similarly, an increase in squalene accumulation in *S. cerevisiae* has been achieved by disruption of one cony of the squalene epoxidase in the diploid. Kamimura, N., Hidaka, M., Masaki, H., and Uozumi, T. (1994) *Appl. Microb. Biotech.* 42: 353-357. The number of copies of squalene epoxidase in *R. glutinis* and *C. curvatus* and other yeasts is determined, and RTDS is used to create or insert a stop codon immediately after the translational start site in extra copies beyond the first one.

In some embodiments, Squalene epoxidase activity is attenuated by addition of terbinafine (an inhibitor of Squalene epoxidase) to the media. In certain embodiments, amino acid changes to the Squalene epoxidase are made to increase the sensitivity of Squalene epoxidase to terbinafine (for example amino acid changes homologous to G30S, L37P, and R269G mapped on *Saccharomyces* ERG1). In some embodiments the amino and changes are made by gene synthesis and replacement of the wild-type gene with the mutant version by homologous recombination. In other embodiments, the changes are introduced into the wild-type gene by RTDS.

HMGR.

Both *Saccharomyces cerevisiae* and mammalian HMGR enzymes contain amino acid sequences in their linker regions which are present in many short-lived proteins that are subject to rapid intracellular turnover in eukaryotes (see Rogers, S., Wells, R., and Rechsteiner, M. (1986) *Science* 234: 364-368; and Chun, K. T., and Simoni, R. D. (1991) *J. Biol. Chem.* 267(6): 4236-4246). Similar sequences, if present, are identified in the HMGR genes in *Y. lipolytica*, *R. glutinis* and/or *C. curvatus*, and eliminated using RTDS to reduced HMGR protein turnover. Such similar sequences have been found in the *S. cerevisiae* squalene synthase gene, and it is also determined if such sequences are present in the squalene synthase genes in *Y. lipolytica*, *R. glutinis* and/or *C. curvatus*. The sequences, if present in *Y. lipolytica*, *R. glutinis* and/or *C. curvatus* squalene synthase, are also eliminated using RTDS to reduce protein turnover.

HGMR in *S. cerevisiae* comprises two highly conserved domains, of which the N-terminal 552 amino acids are responsible for membrane association. Overexpression of the truncated HMG1 protein containing only the C-terminal catalytic portion led a 40-fold increase of HMG-CoA activity in *S. cerevisiae* with an increased accumulation of squalene to 5.5% of dry matter (Polakowski, T., Stahl, U., and Lang, C. (1998) *Appl. Microbiol. Biotech.* 49:66-71). It is determined if *Y. lipolytica*, *R. glutinis* and *C. curvatus* HMGR proteins have a similar structure, and, if so, fragments having only the soluble catalytic domain may be expressed.

The protein structure and DNA sequence of HMGR is highly conserved between eukaryotes from fungi to mammals, with a membrane-associated N-terminal domain and catalytic C-terminal domain. The boundary between the two domains can be mapped to a region of amino acids 500-600 in the *Yarrowia lipolytica* HMG1 gene (Genelouvres *Yarrowia lipolytica* YAL10E04807g) where the hydrophobicity plot transitions from hydrophobic to hydrophilic. Resides 548 and 544 are chosen from evaluation of the hydrophobicity plot of *Yarrowia Lipolytica* HGM1, and its homology to the N-termini of the truncated *Saccharomyces cerevisiae* (Donald, K. A. G., et al, 1997. *Appl. Environ. Micro.* 63(9):3341-3344) and *Candida utilis* (Shimada, H. et al. 1998. *Appl. Environ. Micro.* 64(7):2676-2680) proteins. Accordingly, in one example, amino acids 548-1000 of the C-terminal domain of *Yarrowia lipolytic* HGM1 I is expressed; in a second example amino acids 544-1000 of the C-terminal domain *Yarrowia lipolytica* HMG1 I is expressed. In related examples, amino acids 543-1000 of the C-terminal domain of *Yarrowia lipolytica* HGM1 I is expressed; or amino acids 545-1000 of the C-terminal domains of *Yarrowia lipolytica* HGM1 I is expressed; or amino acids 546-1000 of the C-terminal domains of *Yarrowia lipolytica* HMG1 I is expressed; or amino acids 547-1000 of the C-terminal domains of *Yarrowia lipolytica* HMG1 I is expressed; or amino acids 549-1000 of the C-terminal domains of *Yarrowia lipolytica* HMG1 I is expressed.

Expression of the 457 amino-acid C-terminal catalytic domain of HMGR (resides 543-1000) in *Y. lipolytica* strain Polg yielded 2% squalene/total lipid compared to 0% in the control strain containing the vector alone in experiments using shakeflasks. The process is repeated and expanded using fermenters.

In Syrian hamsters, activity of the HGMR catalytic domain is down-modulated by phosphorylation by an AMP-dependent kinase (Omkumar, R. V., Darnay, B. G., and Rodwell, V. W. (1994) J. Biol. Chem. 269:6810-6814), and a similar mode of regulation has been described in *S. cerevisiae*. It is determined if the HMGR proteins in *R. glutinis, C. curvarus* and other yeasts are similarly regulated, and if so, RTDS is employed to eliminate the phosphorylation site.

Squalene Synthase.

Squalene synthase in mammalian systems is coordinately regulated on the transcriptional level along with HMG-CoA synthase and farnesyl diphosphate synthase by SREBPs (sterol regulatory element binding proteins) (Szkopinsda, A., Swiezewska, E., and Karst, F (2000) Biochem. Biophys. Res. Comm. 267:473-477). SREBPs exist in three forms, of which one binds the squalene synthase promoter. It is determined if such transcription factors and/or binding sites are present on the squalene synthase promoter in *R. glutinis, C. curvatus* and other yeasts, and, it present, RTDS is used to make changes to such transcription factors and/or binding sites that enhance transcription of squalene synthase.

Overexpression of the *Y. lipolytica* Squalene Synthase in *Y. lipolytica* strain Polg yielded 2% squalene/total lipid compared to 0% in the control strain containing the vector alone using shakeflasks. The process is repeated and expanded using fermenters.

Example 5

Growth Conditions for *Cryptococcus curvatus*

*Cryptococcus curvatus* growth was evaluated to determine the best carbon sources to maximize its cell mass in culture. In a Yeast Extracted-based rich media (10 g/L yeast extract, 20 g/L peptone), *C. curvatus* grew well in 2-20% w/v glucose, achieving a maximal level of 55 g/L cell dry weight (CDW) at 16% w/v glucose and above after 4 days. Similarly, *C. curvatus* grew in the same media with 3-12% w/v glycerol, achieving a CDW of 40 g/L in 12% w/v glycerol after 5 days. *C. curvatus* was also grown in Biodiesel glycerol (Imperial Western Products, Coachella, Calif.) up to 3.5% w/v, resulting in 23 g/L CDW.

Example 6

Environmental Manipulation of Target Genes for Increased Squalene Production

Environmental manipulations are tested to increase the net yield of squalene. These include (a) inhibiting ACCase expression and/or activity with oleic acid, olive or other vegetable oil(s), inositol, choline, soraphen, fluazifop, and clethodim or other ACCase inhibiting herbicides, (b) inhibiting squalene epoxidase expression and/or activity with terbinafine, tolnaftate, and ergosterol or other squalene epoxidase inhibiting fungicides, (c) manipulating the C/N ratio in glycerol-based media (in the starting media or by add-ins), (d) varying the nitrogen source in the media (organic vs. inorganic vs. simple/complex), (e) varying carbon addition regimes (e.g. batch vs. feeding), (f) examining the effect of depleting nutrients other than carbon source, (g) varying the carbon source to include mixtures of sugars, sugar alcohols, alcohols, polyalcohols, and organic acids, (h) selecting for growth on HMGR-inhibitory compounds such as lovastatin or other statin-type inhibitors, and (i) selecting for high oil production in culture using lipophilic dyes or stains and/or by analyzing for extractable lipids using, for example, gravimetric or gas chromatographic methods.

For example, *Yarrowia lipolytica* ATCC 90904 was cultivated in high Carbon/Nitrogen ratio media (C/N=420, Li, Y-H., Liu, B., Zhao, Z-B., and Bai, F-W., 2006 "Optimized Culture Medium and Fermentation Conditions for Lipid Production by *Rhodosporidium torulodies*" Chinese Journal of Biotechnology 22(4): 650-656) (hereafter "CYM001 Media") supplemented with 0 to 50 µg/ml terbinafine at 30° C., 300 rpm for 120 h. Concentrations of 12.5 µg/ml or higher of terbinafine resulted in up to 18.5% of total lipid as squalene.

Various *Yarrowia lipolytica* strains are used for lipid and squalene production including ATCC 20688, ATCC 90811, ATCC 90904, ATCC 90812, ATCC MYA-2613, and Yeastern polg. For example, *Yarrowia lipolytica* strain polg (Yeastern) was cultivated in high Carbon/Nitrogen ratio media (C/N=420, Li, Y-H., Liu, B., Zhao, Z-B., and Bai, F-W. 2006 "Optimized Culture Medium and Fermentation Conditions for Lipid Production by *Rhodosporidium toruloides*" Chinese Journal of Biotechnology 22(4): 650-656) (hereinafter "CYM001 Media") supplemented with 0 to 50 µg/ml terbinafine at 30° C., 300 rpm for 120 h. Concentrations of 12.5 µg/ml or higher of terbinafine resulted in up to 38% of total lipid as squalene and Values of total lipid/Cell Dry weight of up to 51% were achieved.

In another example, *Yarrowia lipolytica* ATCC 90904 was cultivated in CYM001 media supplemented with 0 to 50 µg/ml Oleic acid at 30° C., 300 rpm for 120 h. Supplementation with 10 µl/ml Oleic acid was found to improve lipid accumulation 10-fold in lipid/CDW (cell dry weight) over no supplementation.

In a further example, *Yarrowia lipolytica* ATCC 90904 was cultivated in CYM001 media supplemented with 0 to 200 µM clethodim at 30° C., 300 rpm for 120 h. Supplementation of 200 µM clethodim resulted in a 60-fold increase in the yield (mg) of squalene per 60-ml flask.

Increased oxygen has been shown to cause the differential regulation of HGM1 and HMG2 in *S. cerevisiae*, resulting in rapid degradation of HMG2 and increased expression of HMG1 under aerobic conditions (Casey, W. M., Keesler, G. A., Parks, L. W. (1992) J. Bact. 174:7283-7288). It is determined if the number of HMGR genes in our oleaginous yeasts is affected by oxygen and, if so, their expression and activity is manipulated in the fermenter by altering oxygen levels.

Starting with "CYM001 Media" (Li, Y-H., Liu, B., Zhao, Z-B., and Bai, F-W. (2006) Chinese Journal of Biotechnology 22(4):650-656), various components and concentrations of components are changed (including the addition of new components) to improve cell growth, percent total lipid content/unit mass of cells, and percent squalene/total lipid. Media components that are evaluated include: carbon sources: glycerol, glucose, nitrogen sources: ammonium compounds, nitrates, amino acids, mineral salts: potassium, magnesium, sodium, iron, manganese, zinc, calcium, copper, yeast extract, lipid precursors and lipid synthesis affects: terbinafine, clethodim, oleic acid, palmitoleic acid, linoleic acid, linolenic acid and antifoaming agents. Other factors that are evaluated include: percent inoculum, elapsed fermentation time, temperature, pH, back pressure, dissolved oxygen (DO), feed composition, feed strategy and agitation strategy.

Example 7

Strain Selection

Traditional strain selection methods are used in oleaginous yeasts to increase their net squalene productivity. Strains mutagenized by UV, nitrosoguanidine, or ethane methyl sulfonate are screened and/or selected for increased squalene accumulation. Strains are also subjected to iterative selection pressure, such as repeated passage on YEP (15 g/L yeast extract, 5 g/L peptone) media containing 3% glycerol or media containing lovastatin and other known HMGR inhibitors. Strains are also subjected to repeated passage on CYM001 Media containing varying amounts of glycerol and/or glucose or media containing lovastatin and/or other known HMGR inhibitors, and/or squalene synthase inhibitors to obtain spontaneous mutants with increased HMGR and/or squalene synthase activity. Such mutations may be in HMGR, squalene synthase, or other genes ("secondary site mutations").

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognised that various modifications are possible within the scope of the invention claimed.

Thus, it should be understood that although the invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the Narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

That which is claimed is:

1. A method of producing squalene by a yeast, said method comprising cultivating said yeast with an antifungal agent; wherein the yeast is a *Yarrowia lipolytica* strain selected from the group consisting of ATCC 20688, ATCC 90811, ATCC 90904, ATCC 90812, ATCC MYA-2613, or Yeastern polg, wherein the antifungal agent is an allylamine antifungal agent, and wherein the yeast expresses an exogenous squalene synthase gene, thereby genetically altering the yeast.

2. The method of claim 1, wherein the yeast is a genetically converted yeast and wherein the method comprises increasing or decreasing activity or expression of one or more enzymes in the isoprenoid biosynthesis pathway, wherein said enzyme activity or expression is increased or decreased by one or more designed mutations, wherein said one or more designed mutations are at defined positions within said enzyme, wherein said genetically converted yeast produces increased quantities of isoprenoid as compared to the native yeast.

3. The method of claim 1, wherein the antifungal agent is an allylamine antifungal agent at a concentration between 10 to 15 µg/ml.

4. The method of claim 2, wherein said one or more enzymes are mutated with gene repair oligonucleobases.

5. The method of claim 4, wherein said gene repair oligonucleobase is selected from the group consisting of mixed duplex oligonucleotides, non-nucleotide containing molecules, and single stranded oligodeoxynucleotides.

6. The method of claim 5, wherein said gene repair oligonucleobase is a mixed duplex oligonucleotide.

7. The method of claim 6, wherein said mixed duplex oligonucleotide is fewer than 100 nucleotides but more than 50 nucleotides.

8. The method according claim 5, wherein the first and second strands of the mixed duplex oligonucleotide contain two regions that are homologous with two fragments of the target gene.

9. The method according to claim 2, wherein said one or more enzymes include an enzyme selected from the group consisting of acetyl-CoA carboxylase ("ACCase"), HMG-CoA reductase, squalene epoxidase, squalene synthase, ATP citrate lyase, ATP citrate synthase, mevalonate kinase, glycerol kinase and 5-aminolevulinate synthase.

10. The method according to claim 9, wherein said acetyl-CoA carboxylase has reduced activity or expression.

11. The method according to claim 9, wherein said HMG-CoA reductase has increased activity or expression.

12. The method according to claim 9, wherein said squalene epoxidase has reduced activity or expression.

13. The method according to claim 9, wherein said squalene synthase or ATP citrate lyase has increased activity or expression.

14. The method according to claim 9, wherein said ATP citrate synthase has increased activity or expression.

15. The method according to claim 9, wherein said mevalonate kinase has increased activity or expression.

16. The method according to claim 9, wherein said glycerol kinase has increased activity or expression.

17. The method according to claim 9, wherein said 5-aminolevulinate synthase has reduced activity or expression.

* * * * *